United States Patent [19]

Turner

[11] 4,143,112
[45] Mar. 6, 1979

[54] METHOD FOR MAKING PROBE COVERS FOR ELECTRONIC THERMOMETERS

[75] Inventor: Robert B. Turner, Weymouth, Mass.

[73] Assignee: Johnson & Johnson, New Brunswick, N.J.

[21] Appl. No.: 474,419

[22] Filed: May 30, 1974

[51] Int. Cl.² ............................ B29C 27/22; B29F 5/00
[52] U.S. Cl. .................................... 264/249; 264/274; 264/275; 264/320
[58] Field of Search ................ 264/249, 320, 322, 271, 264/296, 319, 342, 345, 230, 288, 291, 292, 259, 274, 275; 156/293, 85, 69

[56] References Cited

U.S. PATENT DOCUMENTS

| 339,812 | 4/1886 | Ritchie | 29/511 |
|---|---|---|---|
| 2,120,806 | 6/1938 | Keuffel | 29/516 |
| 2,257,566 | 9/1941 | Lewis | 29/511 |
| 2,507,638 | 5/1950 | Leahy | 264/249 |
| 2,671,889 | 3/1954 | Vickery | 264/230 |
| 3,050,786 | 8/1962 | St. John et al. | 264/230 |
| 3,189,672 | 6/1965 | Lyman | 264/249 |
| 3,435,109 | 3/1969 | Flaming | 264/322 |
| 3,470,604 | 10/1969 | Zenick | 264/249 |
| 3,491,181 | 1/1970 | Keil et al. | 264/249 |
| 3,557,278 | 1/1971 | Kuhlemann | 264/322 |
| 3,597,372 | 8/1971 | Cook | 264/230 |
| 3,634,924 | 1/1972 | Blake et al. | 264/230 |

FOREIGN PATENT DOCUMENTS

| 418429 | 7/1910 | France | 29/516 |
|---|---|---|---|
| 15545 of | 1901 | United Kingdom | 29/511 |
| 607828 | 9/1948 | United Kingdom | 264/230 |

Primary Examiner—W.E. Hoag

[57] ABSTRACT

Method of installing a tip on a tube for making a probe cover comprising: axially, movably supporting the tube on an axially movable support pin with the pin extending beyond the end of the tube; placing a tip on the end of the pin that extends beyond the tube; applying a force to the tip to engage the tip with the end of the tube; applying a force to the end of the tube engaged with the tip to curl that end of the tube inwardly about the tip; and applying heat to the tip to soften that end of the tube engaged with the tip and cause it to reform about the tip in the inwardly curled form induced by the force applied to the end of the tube.

1 Claim, 10 Drawing Figures

FIG. 1.  FIG. 2.
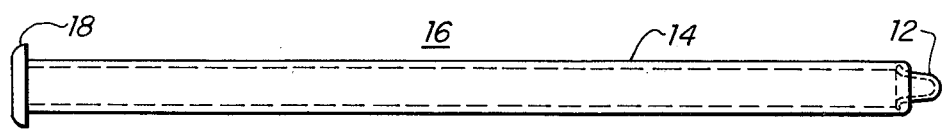
FIG. 3.
FIG. 4.
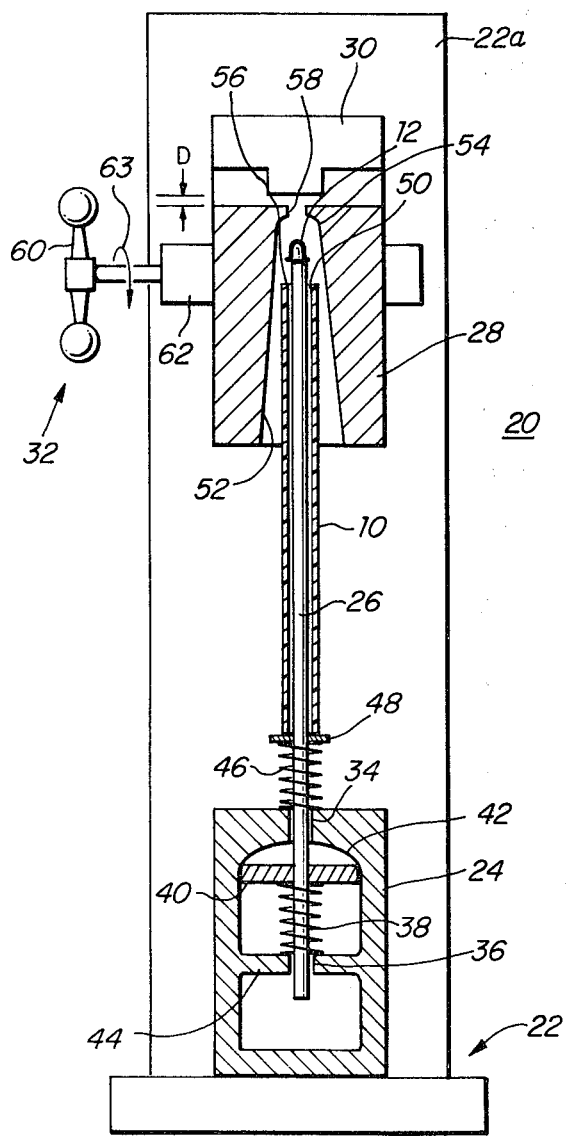
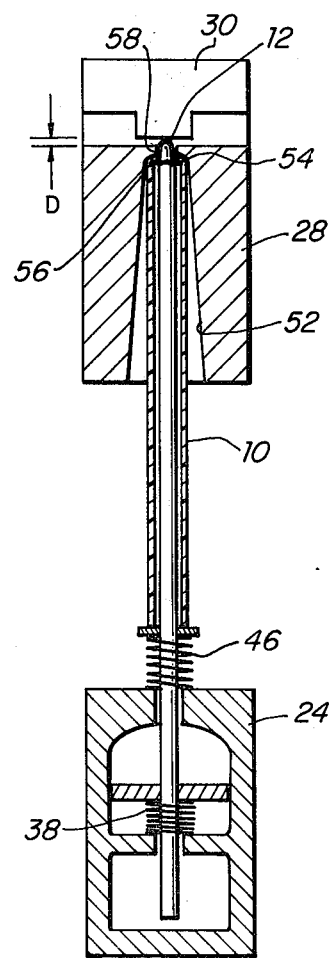
FIG. 5.  FIG. 6.

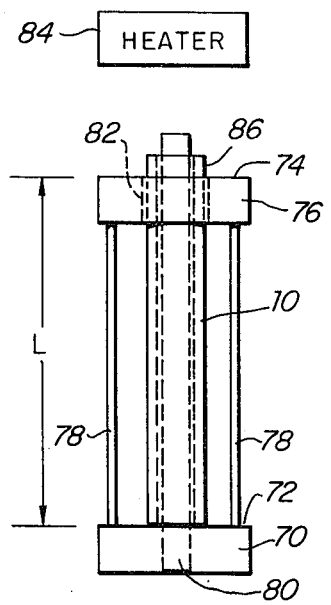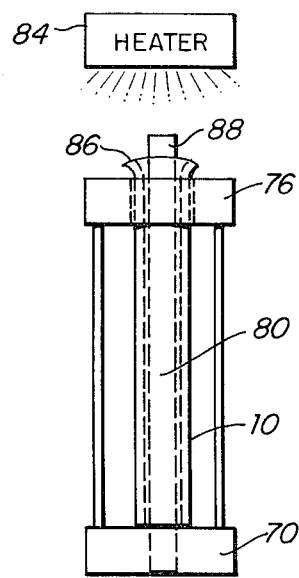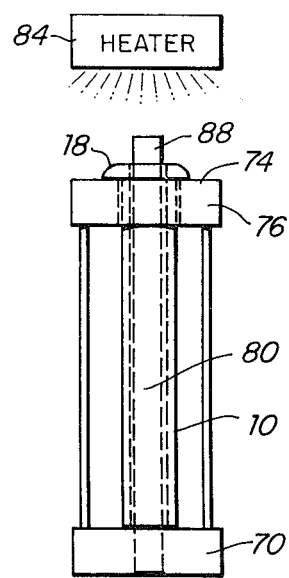
FIG. 7.   FIG. 8.   FIG. 9.
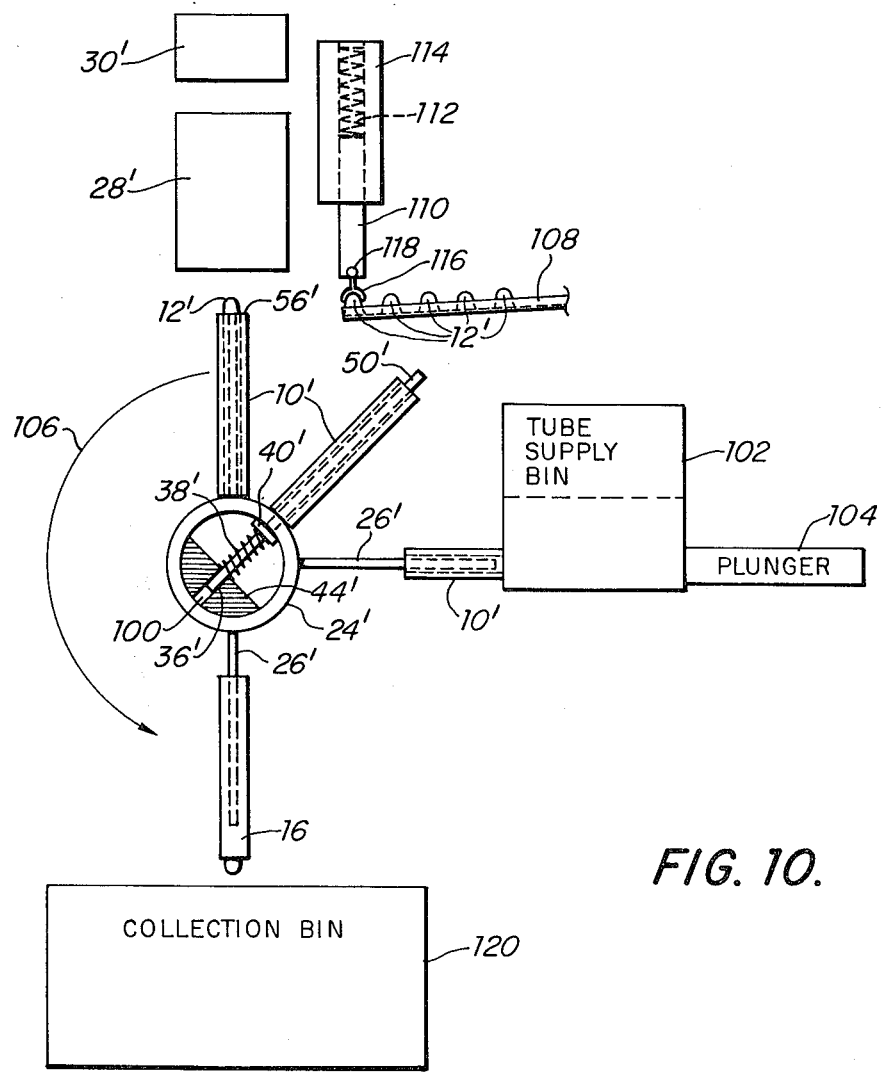
FIG. 10.

METHOD FOR MAKING PROBE COVERS FOR ELECTRONIC THERMOMETERS

FIELD OF INVENTION

This invention relates to an improved method and apparatus for making a disposable probe cover for an electronic thermometer system.

BACKGROUND OF INVENTION

Electronic thermometers are becoming ever more widely used especially in the field of medicine and patient care. Although such thermometers are initially relatively expensive compared to mercury thermometers, they are comparable in overall cost to mercury thermometers when the electronic thermometers are used with disposable probe covers, and further, when the breakage costs and routine sterilization costs of mercury thermometers are considered. Electronic thermometers are capable of much faster temperature measurement which significantly reduces the time required of costly and scarce medical personnel. Probe covers are a significant portion of the operating costs of electronic thermometers. One conventional technique for manufacturing them employs injection molding techniques which utilize very expensive machines and dies and require costly skilled labor. In addition injection molding techniques require that the probe covers have a certain minimum wall thickness which is in excess of that required for its function as a probe cover.

SUMMARY OF INVENTION

It is therefore an object of this invention to provide a simple and inexpensive method for making probe covers.

It is a further object of this invention to provide such a method which reduces the amount of material used to make each probe cover.

It is a further object of this invention to provide a simple and inexpensive apparatus for making probe covers.

It is a further object of this invention to provide such an apparatus which reduces the amount of material used to make each probe cover.

The invention features a technique for installing a tip on a tube to form an electronic thermometer probe cover. Initially a tube is supported on an axially movable support pin with the pin extending beyond one end of the tube. A tip is installed on the end of the pin that extends beyond the tube and a force is applied to the tip to engage the tip with the end of the tube. A force is also applied to the end of the tube engaged with the tip to curl that end of the tube inwardly about the tip. Heat is applied to the tip to soften the end of the tube engaged with the end of the tip to cause it to reform about the tip in the inwardly curled form induced by the force supplied to the end of the tube.

In a preferred embodiment the technique further includes forming a flange on the tube by installing a precut section of tube on a pin within a hole in the die member, with the first end of the pin extending a first predetermined distance beyond the die member in one direction and a second predetermined distance beyond the die member in a second direction. Heat is applied to the second end of the tube extending beyond the die member in the second direction to cause that end of the tube to expand and turn outwardly from the pin and downwardly toward the die member to form a flange.

The invention simultaneously features apparatus for forming an electronic thermometer probe cover from a piece of tube including apparatus for installing a tip in a piece of tube. There is a pin member for receiving the tube and for holding a tip at its free end. A mounting block receives the other end of the pin member and includes a first biasing device for urging the pin member outwardly of the mounting block and a second bias device for urging the tube installed on the pin member away from the mounting block. A forming member has a cavity contoured for inwardly curling the end of the tube about the tip and there is a hole in the cavity for gripping the tip. A drive system urges the forming member toward the end of the tube to engage the tip with the end of the tube. The heater device heats the tip and the end of the tube and causes the end of the tube to soften and reform about the tip in the inwardly curled form induced by the cavity contour.

In a preferred embodiment the apparatus also includes a first stop member having a first surface for abutting a first end of the tube, a die member having a hole for receiving the second end of the tube, a pin member for receiving the tube and extending from the first surface of the stop member through the first surface, a hole, and the second surface, successively, of the die member and beyond the second surface. The second surface of the die member and the first surface of the stop member are spaced apart by a predetermined distance. A heater device heats the second end of the tube extending beyond the second surface to cause the second end to turn outwardly from the pin member and downwardly towards the second surface and form a flange.

DISCLOSURE OF PREFERRED EMBODIMENT

Other objects, features and advantages will occur from the following description of a preferred embodiment and the accompanying drawings, in which:

FIG. 1 is a side view of a piece of tubing which may be formed into a probe cover according to this invention;

FIG. 2 is a tip which may be fitted into one end of the tube shown in FIG. 1 to form a probe cover according to this invention;

FIG. 3 illustrates the tube of FIG. 1 combined with the tip of FIG. 2 to form a probe cover according to this invention;

FIG. 4 illustrates the probe cover of FIG. 3 with a flange formed at one end;

FIG. 5 discloses an apparatus for installing a tip in a tube according to this invention;

FIG. 6 is a simplified diagram of the apparatus of FIG. 5 with the tip in the tube being formed together;

FIG. 7 is a diagram of an apparatus for forming a flange on one end of a tube according to this invention;

FIG. 8 is a diagram of the apparatus of FIG. 7 in the initial stage of the flange forming operation;

FIG. 9 shows the final stage of the flange forming operation carried out with the apparatus of FIG. 7; and FIG. 10 is a diagram of an alternative apparatus for installing a tip on a tube to form a probe cover according to this invention.

There is shown in FIG. 1 a tube 10 of plastic, typically made by an extrusion process to be very thin walled. Tip 12, FIG. 2, is typically made of aluminum and is hollow having a tapered inner surface 14 which engages with the temperature sensing probe of the electronic thermometer. Probe cover 16, FIG. 3, is made by forming tube 10 with tip 12. In one configuration the probe cover 16 may include a flange 18, FIG. 4, at the opposite end of tube 10 from tip 12 for being engaged with the gripping mechanisms of certain electronic thermometers. Probe cover 16 may be formed using apparatus 20, FIG. 5, which includes a frame 22 which supports mounting block 24, pin 26, forming die 28, heater 30 and a drive mechanism 32 for moving heater 30 and forming die 28 toward and away from mounting block 24.

Mounting block 24 receives pin 26 in bore 34 and inner bore 36. Spring 38 bears against plate 40 fixed to pin 26 urging pin 26 outwardly of block 24. Shoulder 42 in mounting block 24 engages with plate 40 to limit the outward motion of pin 26. Partition 44 engages with plate 40 to limit the inward motion of pin 26. Spring 46 bears on washer 48 to urge tube 10 upwardly on pin 26. The upper end 50 of pin 26 is shaped to fit the inner taper 14, FIG. 2, of tip 12. Forming die 28 includes a cavity 52 contoured specifically in curved area 54 to provide a force on the upper end 56 of tube 10 to curl it inwardly about the upper end 50 of pin 26. Hole 58 in the upper end of cavity 52 is sized to grip tip 12. Heater 30 is fixed at a predetermined distance D from the top of forming die 28. Heater 30 and forming die 28 are moved toward and away from mounting block 24 by means of drive system 32 which includes one or more actuator handles 60 interconnected with a conventional gearing mechanism 62 which is fixed to the back 22a of frame 22 and engages with heater 30 and forming die 28.

In operation tube 10 is placed on pin 26 and then tip 12 is placed on the protruding end of pin 26. Handle 60 is rotated in the direction as shown by arrow 63 causing forming die 28 and heater 30 to move downwardly as shown in FIG. 6. Hole 58 in forming die 28 first grips tip 12 and moves it and pin 26 downwardly engaging it with the upper end 56 of tube 10; then tip 12, pin 26 and tube 10 are moved jointly by forming die 28 against the bias of springs 46 and 38. The force of spring 46 urges the upper end 56 of tube 10 firmly against the curved portion 54 of cavity 52. The downward motion of forming die 28 and heater 30 continues as heater 30 comes in contact with tip 12 and then comes to rest. The heat applied to tip 12 softens the upper end 56 of tube 10 and causes it to conform to shoulder 54 of cavity 52. Handle 60 may then be reversed and tube 10 with tip 12 installed may be removed.

The steps illustrated and explained with respect to FIGS. 5 and 6 may be accomplished with automated machinery rather than the apparatus 20 or may be done entirely by hand. In practice apparatus 20 may include a number of mounting block mechanisms and pins 26 ganged together and operated on by a number of cavities 52 disposed in a single forming die.

Flange 18, FIG. 4, may be formed by placing tube 10 on a support plate 70, FIG. 7, whose upper surface 72 is separated from the upper surface 74 of die plate 76 by one or more rods 78 by the distance L, the desired distance between the flange and the other end of the tube. A pin 80 mounted in support plate 70 extends upwardly through an enlarged bore 82 in die plate 76. Bore 82 is large enough to receive tube 10 mounted on pin 80. Tube 10 extends a predetermined distance beyond surface 74 of die plate 76 in the direction toward support plate 70 and for a shorter distance in the other direction above surface 74.

In operation tube 10 is installed on pin 80 and heater 84 is energized or if already energized is brought closer to the upper end 86 of tube 10 until the heat begins to cause upper end 86 to curl outwardly away from the upper end 88 of pin 80. After a period of time end 86 completely curls over away from end 88 of pin 80 and downwardly toward surface 74 of die plate 76 where it flattens and forms flange 18, FIG. 9. The outward and downward curling which occurs in FIG. 8 is the result of the fact that tube 10 has been formed by an extrusion process in which the final diameter of the tube is obtained by drawing down a larger diameter tube. Memory of stress patterns induced by this action causes end 86 to expand outwardly recalling the larger diameter from which it was drawn.

Heater 84 could be a resistive pad, an infra-red source, an ultra-sonic source or any other conventional heating device.

A continuous method of installing tips 12 on tube 10 is shown in FIG. 10 where like parts have been given like numbers primed with respect to FIGS. 5 and 6. In FIG. 10 mounting block 24' is rotated about an axis 100; mounting block 24' indexes first to a tube supply bin 102 in which a single column stack of tubes 10' is contained. Upon indexing to this position, plunger 104 may be actuated to push one tube 10' onto pin 26'. As mounting block 24' continues to rotate in the direction of arrow 106 the end 50' of pin 26' will engage the lead tip 12' in supply channel 108 drawing it out of supply channel 108 under the pressure of plunger 110 of piston 110 driven by spring 112 in cylinder housing 114. The force of piston 110 is applied to tip 12' through a cup-shaped holder 116 connected by means of a ball joint 118 to the end of piston 110. As pin 26' continues its rotation it indexes to a position beneath heater 30' and forming die 28' which forms the end 56' of tube 10 to tip 12'. Continued rotation brings pin 26' with probe cover 16 over collection bin 120 into which probe cover 16 falls.

The apparatus in FIG. 10 may be made more productive by providing more than one pin 26' about the circumference of mounting block 24' and enlarging it sufficiently so that it may contain all the necessary mechanisms for each of the pins. In such an operation the loading and supply bin 102 and the supply channel 108 and the heating and forming performed by heater 30' and forming die 28' and the collection bin 120 may all be set to perform simultaneously on tubes 10' mounted on different ones of pins 26'. In addition to providing additional pins 26' about the circumference of mounting block 24', mounting block 24' may be axially enlarged in the direction perpendicular to the drawings to accommodate numbers of pins 26' extending axially along it on its circumference. In that case collection bin 120 would be extended in the direction perpendicular to the drawings. Tube supply bin 102 would have a number of partitions dividing it for aligning a number of columns of tubes and plunger 104 would contain a like number of plungers. Similarly there would be a number of supply channels 108 for tips 12', a number of pistons 110 and associated equipment and a number of heaters 30' and forming dies 28'.

Other embodiments will occur to those skilled in the art and are within the following claims:

What is claimed is:

1. A method for forming an electronic thermometer probe cover comprising: providing a closed, metal tip member having a radially extending flange; providing a thermoplastic tube; pressing said tip member into engagement with one end of said tube; disposing a forming die about said one end for curling the end of the tube engaged with the tip inwardly about the tip; applying heat directly to said tip to heat the tip to soften the end of the tube engaged with the tip and, to cause the tube end to be reformed about the flange in an inwardly curled manner, thereby securing said tip to said tube, and forming said probe cover.

* * * * *